United States Patent
Lee

(10) Patent No.: US 11,446,229 B2
(45) Date of Patent: Sep. 20, 2022

(54) SHEAR-THINNING COSMETIC COMPOSITION

(71) Applicant: ELC Management LLC, Melville, NY (US)

(72) Inventor: Wilson A. Lee, Hauppauge, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 17/319,063

(22) Filed: May 12, 2021

(65) Prior Publication Data

US 2021/0353523 A1 Nov. 18, 2021

Related U.S. Application Data

(60) Provisional application No. 63/025,800, filed on May 15, 2020.

(51) Int. Cl.
| | | |
|---|---|---|
| *A61K 8/81* | (2006.01) | |
| *A61K 8/25* | (2006.01) | |
| *A61Q 19/00* | (2006.01) | |
| *A61K 8/73* | (2006.01) | |
| *A61K 8/04* | (2006.01) | |
| *A45D 34/04* | (2006.01) | |
| *A45D 40/26* | (2006.01) | |

(52) U.S. Cl.
CPC .............. *A61K 8/817* (2013.01); *A45D 34/04* (2013.01); *A45D 40/26* (2013.01); *A61K 8/046* (2013.01); *A61K 8/25* (2013.01); *A61K 8/733* (2013.01); *A61Q 19/00* (2013.01); *A45D 2200/057* (2013.01); *A45D 2200/058* (2013.01); *A61K 2800/10* (2013.01); *A61K 2800/30* (2013.01); *A61K 2800/34* (2013.01); *A61K 2800/48* (2013.01); *A61K 2800/87* (2013.01)

(58) Field of Classification Search
CPC ................................ A61A 8/046; A61Q 19/00
See application file for complete search history.

(56) References Cited

U.S. PATENT DOCUMENTS

| | | | |
|---|---|---|---|
| 6,685,978 B1 * | 2/2004 | Hauksson ............ | A23B 4/0235 |
| | | | 426/573 |
| 8,603,505 B2 | 12/2013 | Brown et al. | |
| 2006/0110414 A1 | 5/2006 | Suda et al. | |
| 2008/0317795 A1 * | 12/2008 | Traynor ................ | A61Q 19/10 |
| | | | 424/401 |
| 2011/0200666 A1 | 8/2011 | Teichmuller et al. | |
| 2017/0326044 A1 * | 11/2017 | Springinsfeld .......... | A61K 8/28 |

FOREIGN PATENT DOCUMENTS

| | | |
|---|---|---|
| CN | 109350609 A | 2/2019 |
| WO | WO-2019240556 A1 | 12/2019 |

OTHER PUBLICATIONS

PCT International Search Report; International Application No. PCT/US2021/032105; Completion Date: Aug. 26, 2021; dated Sep. 2, 2021; 19.50.
PCT Written Opinion of the International Searching Authority; International Application No. PCT/US2021/032105; Completion Date: Aug. 26, 2021; dated Sep. 2, 2021; 19.50.
Taiwan IPO Search Report from Taiwan Application No. 110117514; dated May 4, 2022; 19.50.

* cited by examiner

*Primary Examiner* — Gina C Justice
(74) *Attorney, Agent, or Firm* — Tiffany A. Johnson

(57) ABSTRACT

The present invention relates to a shear-thinning or pseudo-plastic cosmetic composition. Zeta potentials may be balanced such that a first ratio of the first zeta potential to the second zeta potential may be approximately 1:2. A second ratio of the first zeta potential to the third zeta potential may be approximately 1:2. And, a third ratio of the second zeta potential to the third zeta potential may be approximately 1:1. Balancing zeta potentials may ensure the shear-thinning cosmetic composition can dispense in its original viscous form and as a fine mist through a single device.

10 Claims, No Drawings

SHEAR-THINNING COSMETIC COMPOSITION

FIELD OF THE INVENTION

The present invention generally relates to a shear-thinning cosmetic composition, and more particularly, to a shear-thinning cosmetic composition having balanced zeta potentials.

BACKGROUND OF THE INVENTION

Compositions having a cream, gel, lotion, or an otherwise viscous consistency can experience challenges dispensing in less viscous forms. Creating a shear-thinning composition, thixotripic in nature, with a continuous phase or decrease in viscosity over time can be challenging. When dispensed under shear stress, conventional shear-thinning compositions can slovenly dispense, such as, by spurting or creating build-up around the nozzle or orifice. As such, conventional viscous compositions lack the capability of achieving a continuous phase sufficient to dispense as a fine mist.

SUMMARY OF THE INVENTION

Embodiments of the present disclosure generally provide a cosmetic composition that may include a first active ingredient having a first zeta potential, a second active ingredient having a second zeta potential, and a third active ingredient having a third zeta potential. A first ratio of the first zeta potential to the second zeta potential may be approximately 1:2. A second ratio of the first zeta potential to the third zeta potential may be approximately 1:2. A third ratio of the second zeta potential to the third zeta potential may be approximately 1:1. A combination of the first active ingredient, the second active ingredient, the third active ingredient, and other ingredients may be delivered through a single device, in its original form, and as a fine mist.

Embodiments of the present disclosure may provide a cosmetic composition that may include a first active ingredient having a first zeta potential, a second active ingredient having a second zeta potential, and a third active ingredient having a third zeta potential. A first ratio of the first zeta potential to the second zeta potential may be approximately 1:2. A second ratio of the first zeta potential to the third zeta potential may be approximately 1:2. A third ratio of the second zeta potential to the third zeta potential may be approximately 1:1. A combination of the first active ingredient, the second active ingredient, the third active ingredient, and other ingredients may be delivered through a single device having one or more nozzles under both a low shear and a high shear.

The foregoing summary is only intended to provide a brief introduction to selected features that are described in greater detail below in the detailed description. Other technical features may be readily apparent to one skilled in the art from the following drawings, descriptions, and claims. As such, this summary is not intended to identify, represent, or highlight features believed to be key or essential to the claimed subject matter. Furthermore, this summary is not intended to be used as an aid in determining the scope of the claimed subject matter.

BRIEF DESCRIPTION OF THE DRAWINGS

None

DETAILED DESCRIPTION OF THE INVENTION

To facilitate an understanding of this invention, several terms are defined below. Terms defined herein have meanings as commonly understood by a person of ordinary skill in the areas relevant to the present invention. Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

As used herein, a "cosmetic agent" or "cosmetic ingredient" or "ingredients" means agents or active ingredients suitable for topical application on mammalian keratinous tissue. The cosmetic agent may be a substance that aids in the cleansing or enhancement or protection of a subject's skin or the appearance (e.g., color, texture, look, feel, etc.) or odor of the subject's skin, body or hair. The cosmetic agent may change the underlying structure of the skin or hair.

As used herein, the terms "prevent" and "preventing" include the prevention of the recurrence, spread, or onset of a skin or hair condition. It is not intended that the present invention be limited to complete prevention.

A "subject" refers to any mammal, preferably a human.

As used herein, the term "topical" refers to the administration of an agent or agents (e.g., cosmetic, vitamin, etc.) on the skin.

The term "zeta potential" refers to the zeta potential is the electric potential at the plane of shear.

Except in operating and comparative examples, or where otherwise explicitly indicated, all numbers in this description indicating amounts or ratios of substrate or conditions of reaction, physical properties of substrates, and/or use are to be understood as modified by the word "about". All amounts are presented as percentages by weight of the final composition unless otherwise specified.

The term "weight percent" may be denoted as "wt. %" herein.

All percentages, parts, and ratios are based upon the total weight of the compositions of the present invention unless otherwise specified. All such weights as they pertain to listed ingredients are based on the active level, and therefore they do not include solvents or by-products that may be included in commercially available materials unless otherwise specified.

The present disclosure generally provides a shear-thinning cosmetic composition capable of dispensing in its original form and as a fine mist. Its original form may be a viscous composition, such as, a gel, lotion, cream, or another viscous composition. A fine mist may be a liquid that may provide particles less than approximately 1 micrometer (μall).

Form of Composition and Other Ingredients

Preferred compositions of the invention are a single aqueous phase and do not contain oil or silicone. Compositions of the invention may typically comprise from approximately 60% to 75% of water by weight of the total composition. This amount of water is that from all sources, such as that in Vinysol 2140L and Daitosol 5000AD. It should be appreciated that there may be more than 75% or less than 65% water by weight without departing from the present disclosure.

After the elimination of several potential ingredients, the following materials were selected to balance the zeta potential of the cosmetic composition, as listed in Table 1 below.

Merquat™ 100 is a 39-44% aqueous solution of Polyquaternium-6 (a highly charged cationic homopolymer of diallyl dimethyl ammonium chloride); available from Lubrizol Corporation.

Acrylates copolymer is commercially available, for example, as Daitosol™ 5000AD from Daito Kasei Kogyo Co. Daitosol 5000AD is a 50% aqueous mixture of acrylates copolymer. Daitosol 5000AD is reported to have a pH of 5.5-7.5, a viscosity of 50-100 mPa-s, a glass transition temperature (Tg) of about −14° C.

Polyglyceryl-2 isostearate is commercially available, for example, as Risorex™ PGIS21 from Kokyu Alcohol Kogyo Co., Ltd.

Water-soluble red algae extract is commercially available, for example, as Gelalg™ SPE from Knowde.

Lithium magnesium sodium silicate is commercially available, for example, as Laponite-XLG XR™ from Eckart America.

It should be appreciated that the remaining ingredients may not provide a zeta potential or may provide a negligible zeta potential of approximately zero. As such, the remaining ingredients do not impact the zeta potential of the cosmetic composition.

The combination of ingredients may provide more than one zeta potential. For example, a first active ingredient, such as Gelalg SPE, having a first zeta potential. The first zeta potential may be equal to approximately half of a second zeta potential of a second active ingredient, such as Laponite XLG XR. In other words, the ratio between the first zeta potential and the second zeta potential may be approximately 1:2. The first zeta potential may also equal approximately half of a third zeta potential of a third active ingredient, such as polyquaternium-6. The first zeta potential may be approximately +24.34 mV. The second zeta potential may be approximately +50.23 mV. The third zeta potential may be approximately +51.10 mV. In other words, the ratio between the first zeta potential and the third zeta potential may be approximately 1:2. It should be appreciated that the first Zeta potential may be less than or greater than +24.34 mV without departing from the present disclosure. It should also be appreciated that the second zeta potential may be less than or greater than +50.23 mV without departing from the present disclosure. It should further be appreciated that the third zeta potential may be less than or greater than +24.34 mV without departing from the present disclosure. The zeta potential of the cosmetic composition may be between −40 and −50 mV.

The zeta potential of human skin is typically approximately −25 mV. Compositions having a zeta potential greater than −25 mV may best adhere to or provide the most efficacious application to users or human skin. The magnitude of the zeta potential indicates the degree of electrostatic repulsion or attraction between particles in a dispersion. A higher magnitude may indicate particles are more likely to remain in suspension and provide greater stability. Generally, a higher zeta potential may provide higher stability of a colloidal system. When a higher surface charge opposes a charge of particles, a repulsion force may be greater than an attractive force. It should be appreciated that a stable state between two atoms provides attraction to one another with a force equivalent to the force to repel one another.

In some embodiments, the ratio of the zeta potential of the ingredients may range from about 1:1 to about 1:10, and most preferably, 13:1 to about 15:1.

The composition zeta potential breaks down a viscosity of the cosmetic composition and the zeta potential ranges from about −5 millivolts to about −90 millivolts, preferably about approximately −46 millivolts (mV) and more preferably about −10 to −70 millivolts (mV).

The combination of the first active ingredient, the second active ingredient, and the third active ingredient are delivered through one or more nozzles of the single device at high shear and at a low shear, ranging from about 1 to 10 Newtons per square meter ($N/m^2$) at room temperature of approximately 20 to 25 degrees Celsius. Viscosity in the range of approximately 100,000 cSt to approximately 500,000 cSt at a high shear of approximately 80 to 120 $N/m^2$ at approximately 20 to 25 degrees Celsius. For example, a lotion may exhibit a low shear of approximately 1 to 10 $N/m^2$ and a mist may exhibit a high shear of approximately 80 to 120 $N/m^2$.

Zeta Potential Measurement.

The combination of the first active ingredient, the second active ingredient, and the third active ingredient have a viscosity ranging from approximately 0 centistokes (cSt) to 15 million cSt, preferably about 0 centistokes (cSt) to 5 million cSt.

The zeta potential is a key indicator of the stability of colloidal dispersions, i.e. creams and lotions. The zeta potential measures the magnitude of the electrostatic or charge repulsion/attraction between particles and is one of the fundamental parameters known to affect the stability of compositions. In other words, the zeta potential is the electric potential at the plane of shear. Measuring the zeta potential provides insight into the causes of dispersion, aggregation, and/or flocculation, and may be applied to improve the formulation of dispersions, emulsions and suspensions.

Generally, the zeta potential of human skin is typically approximately −25 mV. Compositions according to the present invention include a zeta potential greater than −25 mV. Such compositions having the zeta potential may best adhere to or provide the most efficacious application to users or human skin. The magnitude of the zeta potential indicates the degree of electrostatic repulsion or attraction between particles in a dispersion. A higher magnitude may indicate particles are more likely to remain in suspension and provide greater stability. Generally, a higher zeta potential may provide higher stability of a colloidal system. When a higher surface charge opposes a charge of particles, a repulsion force may be greater than an attractive force. It should be appreciated that a stable state between two atoms provides attraction to one another with a force equivalent to the force to repel one another.

The shear-thinning composition of the present invention may be pseudoplastic and may provide a non-Newtonian behavior of fluids. It should also be appreciated that the cosmetic composition may provide a topical formulation with film formers and/or inclusive or exclusive color or colorants without departing from the present disclosure. It should further be appreciated that the cosmetic composition may be a setting primer that may provide a sprayer to deliver a uniform coverage to the skin. It should be appreciated that the output of the spray may be designed to deliver a fine mist to achieve optimum results. It should also be appreciated that a shear-thinning cosmetic composition or a pseudoplastic with high viscosity of the present disclosure may spray at any angle without departing from the present disclosure.

It should be appreciated that the remaining ingredients may not provide a zeta potential or may provide a negligible zeta potential of approximately zero. As such, the remaining ingredients do not impact the zeta potential of the cosmetic composition.

Formulation

According to an aspect of the present invention, the formulation comprising the cosmetic agent may be applied to mammalian keratinous tissue, to human skin, face or hair. The formulation comprising the cosmetic agents may be of various forms. For example, some non-limiting examples of such forms include solutions, suspensions, lotions, creams, gels, emulsions, suspension, toners, ointments, cleansing agents, exfoliating agents, liquid shampoos and hair conditioners, pastes, foams, powders, mousses, shaving creams, hydrogels, film-forming products, facial and skin masks, and the like.

Exposure to ultraviolet light may result in excessive scaling and texture changes of the stratum corneum. Therefore, the cosmetic agents of the subject invention may optionally contain a sunscreen active. As used herein, "sunscreen active" includes both sunscreen agents and physical sunblock. Suitable sunscreen actives may be organic or inorganic.

Inorganic sunscreens useful herein include the following metallic oxides: titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the cosmetic agent.

A wide variety of conventional organic sunscreen actives are suitable for use herein. Sagarin, et al., at Chapter VIII, pages 189 et seq., of Cosmetics Science and Technology (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone, naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2,4,4-tetrahydroxybenzophenone, 2,2-dihydroxy-4,4'-dimethoxybenzophenone, octabenzone; 4-isopropyldibenzoylmethane; butylmethoxydibenzoylmethane; etocrylene; octocrylene; [3-(4'-methylbenzylideneboman-2-one), terephthalylidene dicamphor sulfonic acid and 4-isopropyl-di-benzoylmethane. Of these, 2-ethylhexyl-p-methoxycinnamate (commercially available as PARSOL MCX), 4,4-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and mixtures of these compounds, are preferred.

More preferred organic sunscreen actives useful in the cosmetic agents useful in the subject invention are 2-ethylhexyl-p-methoxycinnamate, butylmethoxydibenzoyl-methane, 2-hydroxy-4-methoxybenzo-phenone, 2-phenylbenzimidazole-5-sulfonic acid, octyldimethyl-p-aminobenzoic acid, octocrylene, and mixtures thereof.

Also, particularly useful in the cosmetic agents are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sun screening agents disclosed therein have, in a single particle, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sun screening agents are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N, N-(2-ethylhexyl)methyl-aminobenzoic acid ester of 2-hydroxy-4-(2-hydroxyethoxy)benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane, and mixtures thereof.

Especially preferred sunscreen actives include 4,4'-t-butylmethoxydibenzoylmethane, 2-ethylhexyl-p-methoxycinnamate, phenyl benzimidazole sulfonic acid, and octocrylene. A safe and effective amount of the organic sunscreen active is used, typically from about 1% to about 20%, more typically from about 2% to about 10% by weight of the cosmetic agent. Exact amounts will vary depending upon the sunscreen or sunscreens chosen and the desired Sun Protection Factor (SPF).

In addition, the topical cosmetic agent may contain conventional cosmetic adjuvants and additives such as preservatives, antioxidants, fatty substances, oils, water, organic solvents, silicones, thickeners, emollients, emulsifiers, sunscreens, defoamers, a surfactant, including a cationic surfactant, a filler, a sequestering agent, an anionic, a cationic, a nonionic or an amphoteric polymer or a mixture thereof, a propellant, an acidifying agent or a basic agent, a dye, a colorant/coloring agent, an abrasive, a skin sensate, an astringent, a pigment or a nano pigment or a combustible pigment, such as for example, without limiting, iron oxides, metallic oxides or any other ingredient typically formulated in cosmetic compositions. Such cosmetic ingredients which are suitable for use in the cosmetic composition of the present invention and which are conventionally used in the skin care industry are described in, for example, the CTFA Cosmetic Ingredient Handbook, Second Edition (1992), but are not limited thereto.

The cosmetic agents of the present invention, without limiting, may be present in form of lotions, milky lotions, creams and oil, oil in emulsions, watery substances, gels, hydrogels, shampoos, hair rinses, hair conditioners, hair creams, hair dyes, hair colors, pre- or post-treatment agents for hair dyeing and coating agents for split hair, etc.

The formulation type of the cosmetic agents of the present invention may be of any type, including solution system, soluble system, emulsion system, gel system, powder dispersing system or water-oil two phase system.

Conventional cosmetic adjuvants which may be suitable as additives are, for example, co-emulsifiers, fats and waxes, stabilizers, thickeners, biogenic agents, film formers, fragrances, dyes, pearlescent agents, preservatives, pigments, electrolytes (for example magnesium sulphate) and pH regulators. Co-emulsifiers are preferably known W/O and also O/W emulsifiers such as polyglycerol esters, sorbitan esters or partially esterified glycerides. Typical examples of fats are glycerides; as waxes which may be mentioned in combination with hydrophilicized growing inter alia beeswax, paraffin wax or microcrystalline waxes.

Metal salts of fatty acids such as magnesium, aluminum and/or zinc stearate can be employed. Suitable thickeners are, for example, crosslinked polyacrylic acids and derivatives thereof, polysaccharides, more especially xanthan gum, guar-guar, agar-agar, alginate and tyloses, carboxymethylcellulose and hydroxy ethylcellulose, and also fatty alcohols, monoglycerides and fatty acids, polyacrylates, polyvinyl alcohol and polyvinylpyrrolidone.

Biogenic active plant extracts, protein hydrolysates and vitamin complexes, for example, to understand. Customary film formers are, for example, hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds.

Suitable preservatives are, for example, formaldehyde solution, p-hydroxybenzoate or sorbic acid. Pearlizing agents, for example, such as ethylene glycol distearic esters come coldistearate, but also fatty acids and fatty acid into consideration.

The dyes suitable for cosmetic purposes, and authorized substances may be used. Such dyes are normally used in concentrations of 0.001 to 0.1 wt %, based on the total mixture. An additional content of antioxidants is generally preferred. Thus, all suitable or customary for cosmetic and/or dermatological applications antioxidants can be used as favorable antioxidants.

The sunscreen compositions of the invention can accordingly be in liquid, paste or solid form, for example as a water-in-oil creams, oil-in-water creams and lotions, aerosol foam creams, gels, oils, grease pencils, dusting powders, sprays or hydroalcoholic lotions.

Use

Another aspect of the present invention is the use for cosmetic purposes, including cosmetic uses such as, but not limited to, preventing and/or treating the signs of aging of the skin and protecting the skin from UV rays.

Other uses also include preventing and/or treating impairment in luminosity, loss of radiance of the complexion, impairment of the surface aspect of the skin, and/or impairment of the grain of the skin and/or for maintaining and/or improving the bio mechanical properties of the skin, and/or for stimulating the energy mechanism of fibroblasts, improve hair, improve texture of hair, improve skin radiance, protect the skin from UV radiation, act as a sunscreen, treat skin's impairments, fine lines, wrinkles, aging, or depuffing.

The composition according to the present invention may be delivered by a device having one or more nozzles to facilitate shear. The device may be a single device and may also facilitate dispensation as a fine spray or a fine mist.

While particular embodiments of the present invention have been illustrated and described, it would be obvious to those skilled in the art that various other changes and modifications may be made without departing from scope of the invention. It is therefore intended to cover in the appended claims all such changes and modifications that are within the scope of this invention.

Examples

Example 1: Cosmetic Composition FORMULA I

| Components | Wt % |
| --- | --- |
| Vinysol 2140L[1] | 3.00 |
| Merquat 100[2] | 0.01 |
| Phenoxetol | 0.80 |
| Daitosol 5000AD[3] | 0.15 |
| Risorex PGIS21[4] | 2.60 |
| Propanediol | 1.00 |
| SD Alcohol | 3.00 |
| Gelalg SPE[5] | 10.00 |
| Citric Acid | 0.05 |
| Glycerine | 2.00 |
| Laponite XLG XR[6] | 3.50 |
| Hyactive 10[7] | 0.30 |
| Potassium Sorbate | 0.25 |
| KF-6100[8] | 0.10 |
| Water | Q.S. |

[1] 60% aqueous mixture of acrylates/VA copolymer/disodium EDTA
[2] polyquaternium-6
[3] 50% aqueous mixture of acrylates copolymer
[4] polyglyceryl-2 isostearate
[5] 90% aqueous mixture of carrageenan
[6] lithium magnesium sodium silicate
[7] sodium hyaluronate
[8] polyglyceryl-3 disiloxane dimethicone Example 2: Cosmetic Composition FORMULA II

| Components | Wt % |
| --- | --- |
| Vinysol 2140L[1] | 3.00 |
| Merquat 100[2] | 0.01 |
| Phenoxetol | 0.80 |
| Daitosol 5000AD[3] | 0.15 |
| Risorex PGIS21[4] | 2.60 |
| Propanediol | 1.00 |
| SD Alcohol | 3.00 |
| Gelalg SPE[5] | 12.00 |
| Citric Acid | 0.05 |
| Glycerine | 2.00 |

-continued

| Components | Wt % |
|---|---|
| Laponite-XLG XR[6] | 4.50 |
| Hyactive 10[7] | 0.30 |
| Potassium Sorbate | 0.25 |
| KF-6100[8] | 0.10 |
| Water | Q.S. |

[1]60% aqueous mixture of acrylates/VA copolymer/disodium EDTA
[2]polyquaternium-6
[3]50% aqueous mixture of acrylates copolymer
[4]polyglyceryl-2 isostearate
[5]90% aqueous mixture of carrageenan
[6]lithium magnesium sodium silicate
[7]sodium hyaluronate
[8]polyglyceryl-3 disiloxane dimethicone Rheology Profile The shear-thinning cosmetic composition may provide a rheology profile that may provide a viscosity in the range of approximately 100,000 centistokes (cSt) to approximately 500,000 cSt at a low shear of approximately 1 to 10 Newtons per square meter ($N/m^2$) at room temperature of approximately 20 to 25 degrees Celsius. Viscosity in the range of approximately 100,000 cSt to approximately 500,000 cSt at a high shear of approximately 80 to 120 $N/m^2$ at approximately 20 to 25 degrees Celsius. For example, a lotion may exhibit a low shear of approximately 1 to 10 $N/m^2$ and a mist may exhibit a high shear of approximately 80 to 120 $N/m^2$.

Zeta Potential Measurement

Example 3: Electric Potential (Hereinafter, "Zeta Potential")

The zeta potential is a key indicator of the stability of colloidal dispersions, i.e. creams and lotions. The zeta potential measures the magnitude of the electrostatic or charge repulsion/attraction between particles and is one of the fundamental parameters known to affect the stability of compositions. In other words, the zeta potential is the electric potential at the plane of shear. Measuring the zeta potential provides insight into the causes of dispersion, aggregation and/or flocculation, and may be applied to improve the formulation of dispersions, emulsions, and suspensions.

The following example includes the zeta potential of each ingredient of a shear-thinning cosmetic composition capable of dispensing both as a fine mist and in its original form and is not intended to be limiting. It should be appreciated that the original form may include, but is not limited to, a gel, cream, lotion, etc. It should be appreciated that a fine mist may provide particles less than approximately 1 μm.

TABLE 1

| Components | Zeta Potential (mV) |
|---|---|
| Vinysol 2140L | * |
| Merquat 100 | +51.10 |
| Phenoxetol | * |
| Daitosol 5000AD | −17.29 |
| Risorex PGIS21 | −61.09 |
| Propanediol | * |
| SD Alcohol | * |
| Gelalg SPE | +24.34 |
| Citric Acid | * |
| Glycerine | * |
| Laponite XLG XR | +50.23 |
| Hyactive 10 | * |
| Potassium Sorbate | * |
| KF-6100 | * |
| Water | * |
| Formula I | −45.99 |
| Formula II | −45.99 |

*It should be appreciated that the zeta potential is minimal or negligible, thereby failing to impact the zeta potential of Formulas I and II.

The combination of ingredients may provide a first active ingredient, such as Gelalg SPE, having a first zeta potential. The first zeta potential may be equal to approximately half of a second zeta potential of a second active ingredient, such as Laponite XLG XR. In other words, the ratio between the first zeta potential and the second zeta potential may be approximately 1:2. The first zeta potential may also equal approximately half of a third zeta potential of a third active ingredient, such as polyquaternium-6. The first zeta potential may be approximately +24.34 mV. The second zeta potential may be approximately +50.23 mV. The third zeta potential may be approximately +51.10 mV. In other words, the ratio between the first zeta potential and the third zeta potential may be approximately 1:2. It should be appreciated that the first Zeta potential may be less than or greater than +24.34 mV without departing from the present disclosure. It should also be appreciated that the second zeta potential may be less than or greater than +50.23 mV without departing from the present disclosure. It should further be appreciated that the third zeta potential may be less than or greater than +24.34 mV without departing from the present disclosure. The zeta potential of the cosmetic composition may be between −40 and −50 mV.

Zeta Potential of Skin

The zeta potential of human skin is typically approximately −25 mV. Compositions having a zeta potential greater than −25 mV may best adhere to or provide the most efficacious application to users or human skin. The magnitude of the zeta potential indicates the degree of electrostatic repulsion or attraction between particles in a dispersion. A higher magnitude may indicate particles are more likely to remain in suspension and provide greater stability. Generally, a higher zeta potential may provide a higher stability of a colloidal system. When a higher surface charge opposes a charge of particles, a repulsion force may be greater than an attractive force. It should be appreciated that a stable state between two atoms provides attraction to one another with a force equivalent to the force to repel one another.

The zeta potential of each active ingredient in Formulas I and II, described hereinabove, was measured using the procedure set forth below.

1. Approximately 49.8 grams of distilled water and approximately 0.2 grams of an active ingredient were placed in a two-ounce container.

2. The container was covered with a lid and sonicated at room temperature for approximately 30 minutes.

3. A capillary cell was inverted, and the sonicated sample was slowly injected from its syringe into the capillary cell to fill a U-tube slightly over approximately 50%.

4. Air bubbles were not formed in the cell.

5. The cell was turned upright and slowly continued injection until the sample was placed at the top of the electrodes or gold metal and monitored again to ensure no bubbles were in the cell. When necessary, the cell was gently tapped to dislodge any bubbles.

6. Both electrodes on the inside of the cell were completely immersed in the sample.

7. A cell stopper was inserted into each port.

8. The cell was loaded into the instrument, and a triangle of the cell was faced forward the front of the nano.

9. The cell was loaded or pushed into the holder until the cell stopped.

10. The measurement chamber lid was closed to cover the cell.

11. The nano and the computer were powered on.

12. Measurements and testing were completed, in accordance with standard operating procedure (SOP).

It should be appreciated that the particle size range may be approximately 0.3 nanometers to approximately −10 micrometers. It should be appreciated that the zeta potential may provide: excellent stability at greater than or equal to approximately 61 millivolts (mV); good stability between approximately 40 and 60 mV; moderate stability between approximately 30 and 40 mV; incipient stability between approximately 10 and 30 mV; and rapid coagulation or flocculation between approximately 0 to 5 mV.

It should be appreciated that the shear-thinning composition may be pseudoplastic and may provide a non-Newtonian behavior of fluids. It should also be appreciated that the cosmetic composition may provide a topical formulation with film formers and/or inclusive or exclusive color or colorants without departing from the present disclosure. It should further be appreciated that the cosmetic composition may be a setting primer that may provide a sprayer to deliver a uniform coverage to the skin. It should be appreciated that the output of the spray may be designed to deliver a fine mist to achieve optimum results. It should also be appreciated that a shear-thinning cosmetic composition or a pseudoplastic with high viscosity of the present disclosure may spray at any angle without departing from the present disclosure.

Instead, unless otherwise specified, each such dimension is intended to mean both the recited value and a functionally equivalent range surrounding that value. For example, a dimension disclosed as "40 mm" is intended to mean "approximately 40 mm."

It may be advantageous to set forth definitions of certain words and phrases used in this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A shear-thinning cosmetic composition, comprising:
    a first active ingredient having a first zeta potential, wherein the first active ingredient is 90% aqueous mixture of carrageenan;
    a second active ingredient having a second zeta potential, wherein the second active ingredient is lithium magnesium sodium silicate; and
    a third active ingredient having a third zeta potential, wherein the third active ingredient is polyquaternium-6;
        wherein a first ratio of the first zeta potential to the second zeta potential is approximately 1:2,
        wherein a second ratio of the first zeta potential to the third zeta potential is approximately 1:2,
        wherein a third ratio of the second zeta potential to the third zeta potential is approximately 1:1,
        wherein the shear-thinning cosmetic composition provides a viscosity in the range of approximately 100,000 centistokes (cSt) to approximately 500,000 cSt at a low shear of approximately 1 to 10 N/m$^2$ at room temperature of approximately 20 to 25 degrees Celsius; and
        wherein the shear-thinning cosmetic composition exhibits a mist form at a high shear of approximately 80 to 120 N/m$^2$.

2. The shear-thinning cosmetic composition of claim 1, wherein the shear-thinning cosmetic composition is delivered through the single device via one or more nozzles.

3. The shear-thinning cosmetic composition of claim 1, wherein the shear-thinning cosmetic composition is delivered through the single device under a shear stress.

4. The shear-thinning cosmetic composition of claim 1, wherein the first active ingredient, the second active ingredient, and the third active ingredient are shear sensitive materials.

5. The shear-thinning cosmetic composition of claim 1, wherein a shear-thinning cosmetic composition zeta potential breaks down a viscosity of the cosmetic composition.

6. The shear-thinning cosmetic composition of claim 5, wherein the shear-thinning cosmetic composition zeta potential is approximately −10 to −70 millivolts (mV).

7. The shear-thinning cosmetic composition of claim 1, wherein the shear-thinning cosmetic composition is delivered through one or more nozzles of the single device at a high shear and at a low shear.

8. The shear-thinning cosmetic composition of claim 1, further comprising a thickener.

9. The shear-thinning cosmetic composition of claim 1, further comprising a film former.

10. The shear-thinning cosmetic composition of claim 1, further comprising a cationic surfactant.

* * * * *